US006168573B1

(12) United States Patent

Fielding et al.

(10) Patent No.: US 6,168,573 B1
(45) Date of Patent: Jan. 2, 2001

(54) HUMAN APPLICATIONS OF CONTROLLED STRESS

(76) Inventors: Stuart Fielding, 16 Bromleigh Way, Morris Plain, NJ (US) 07950; John W Stein, 4 Lois Ct., Hackettstown, NJ (US) 07840

( * ) Notice: Under 35 U.S.C. 154(b), the term of this patent shall be extended for 0 days.

(21) Appl. No.: 09/147,819

(22) PCT Filed: Sep. 12, 1997

(86) PCT No.: PCT/US97/16451

§ 371 Date: Aug. 20, 1999

§ 102(e) Date: Aug. 20, 1999

(87) PCT Pub. No.: WO98/10732

PCT Pub. Date: Mar. 19, 1998

Related U.S. Application Data

(60) Provisional application No. 60/026,007, filed on Sep. 12, 1996.

(51) Int. Cl.[7] .......... A61B 5/00

(52) U.S. Cl. .......... 600/594

(58) Field of Search .......... 600/587, 594, 600/595

(56) References Cited

U.S. PATENT DOCUMENTS 4,022,189 * 5/1977 Boxer .
4,590,939 * 5/1986 Sakowski .
4,686,968 * 8/1987 Scherger .
5,205,238 * 4/1993 Boice .
5,224,469 * 7/1993 Mocny .
5,245,989 * 9/1993 Simon .
5,254,087 * 10/1993 McEwen .
5,290,307 3/1994 Choy .......... 606/204

FOREIGN PATENT DOCUMENTS

90/14128 * 11/1990 (WO) .
96/15755 * 5/1996 (WO) .

* cited by examiner

*Primary Examiner*—Max Hindenburg
(74) *Attorney, Agent, or Firm*—Nixon & Vanderhye P.C.

(57) ABSTRACT

An effect analogous to a tail-pinch effect is evoked in humans by apparatus for applying variable localized pressure to the spine. Control of the pressure can be accomplished manually, by remote control and/or automatically. By selectively applying pressure a number of changes can be evoked in the human including, for example, causing an increase in appetite, a change in sexual behavior, increased blood flow to brain, and/or an increase of neurotransmitters, including dopamine, serotonin and norepinephrine. The effect is useful in treating Parkinson's disease, depressive disorders, stroke and other conditions.

17 Claims, 4 Drawing Sheets

HUMAN APPLICATIONS OF CONTROLLED STRESS

CROSS REFERENCE TO RELATED APPLICATIONS

This application claims priority from Provisional Patent Application Ser. No. 60/026,007 filed Sep. 12, 1996 entitled HUMAN APPLICATIONS OF CONTROLLED STRESS BEHAVIOR which is incorporated herein by reference in its entirety and PCT/US97/16451 filed Sep. 12, 1997.

BACKGROUND OF THE INVENTION

1. Field of the Invention

The invention relates to a human analog to the tail pinch effect utilized in animals and, more particularly, to methods, apparatus, systems and techniques for modifying human behavior, for treating certain diseases and affecting other human conditions.

2. Prior Art

The tail-pinch effect is know from the prior art and its impact on animals is discussed in the literature.

U.S. Pat. No. 5,205,238 to Harry E. Boyce, which issued on Apr. 27, 1993 is entitled METHOD AND APPARATUS FOR INDUCING CONTROLLED STRESS BEHAVIOR IN ANIMALS, SUCH AS ENHANCED EATING, DRINKING, MATING, MATERNAL OR THE LIKE BEHAVIOR. That patent discloses methods and apparatus for applying controlled stress to animals by mounting an apparatus on a body part of an animal and applying variable stress such as a tail pinch. Devices of the type shown in that patent are sometimes referred to as "ABM™" devices. That patent is hereby incorporated by reference in its entirety herein.

However, the prior art does not deal with applying tail-pinch techniques or an ABM type device to humans.

SUMMARY OF THE INVENTION

The present invention extends that which has been done in the prior art to demonstrate an analogous tail-pinch effect in humans. As discussed more hereinafter, the invention permits treatment of Parkinson's disease, depressive disorders and stroke, in addition to a variety of other human conditions.

The invention is directed to apparatus for applying controlled stress by applying variable localized pressure to a human body, including a pressure actuator to apply pressure against a portion of a human body, and a length of flexible material holding said pressure actuator against human body even when pressure is applied.

The invention is also directed to a system for applying variable localized pressure to a human body, including a pressure actuator to apply pressure against a portion of a human body, and a remote control for sending one or more control signals to said pressure actuator over a communications link.

The invention is also directed to a method of applying variable localized pressure to a human body, by positioning a pressure actuator against a portion of the human spine; and selectively applying pressure to the spine using said actuator.

The invention is also directed to a method of causing an increase in appetite, a change in sexual behavior, increased blood flow to brain, and/or an increase of neurotransmitters in the brain in the body of a human being, by positioning a pressure actuator against a portion of the human spine; and selectively applying pressure to the spine using said actuator. The neurotransmitters can be one or more of dopamine, serotonin and norepinephrine.

The invention is also directed to treating Parkinson's disease, depressive disorders and stroke by positioning a pressure actuator against a portion of the human spine; and selectively applying pressure to the spine using the actuator.

The foregoing and other features, aspects and advantages of the present invention will become more apparent from the following detailed description of the present invention when taken in conjunction with the accompanying drawings.

BRIEF DESCRIPTION OF THE DRAWINGS

The objects, features and advantages of the system of the present invention will be apparent from the following description in which.

DETAILED DESCRIPTION OF THE INVENTION

Figure 1A:
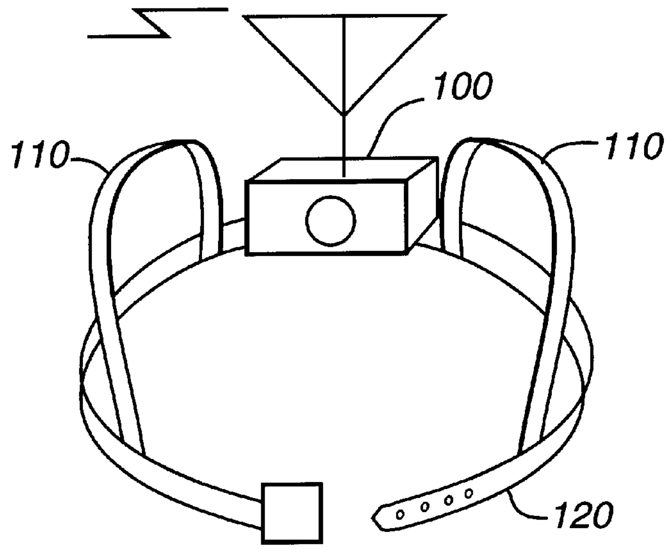
FIG. 1A is an illustration of an exemplary mounting harness for securing a stress inducing device to a human body.

A pressure activator is contained in a belt which the patient wears around the waist, with the stimulation mechanism such as a pressure head comfortably positioned against the spinal cord. The stimulation pressures can be regulated personally by the patient. This approach to therapy delivery permits patients to be able to personally control the "dose" being administered based on the current level of need. Initial pilot studies using prototypes have resulted in a high level of patient acceptance and compliance. Therefore, not only is the therapy effective against disease, but the product will be accepted by the patient.

Initial investigation into uses for devices based on the technology described herein indicates these devices stimulate the release of certain chemicals in the brain which are essential for therapy and/or control of such conditions as Parkinson's Disease, depression, and stroke. This extension of the prior art technology provides effective, non-drug therapies which will compliment or be superior to presently available drugs for some disease conditions and, in others provides therapy for which drugs are not now available. The device will be fitted in a belt worn around the waist, so that the simulator is located along the spine. A personal control feature will allow the patient to increase or decrease the stimulation level. Consequently, Instead of being "chained" to the built-in effects of a drug at a given dosage level, patients will be able to increase or decrease the "dose" of stimulation required at any given time. This feature adds enormous value.

In 1973, Dr. Antelman and Henry Szechtman, Ph.D. (Department of Biomedical Sciences, McMaster University, Ontario, Canada), discovered that application of a mild, non-painful pressure to the tails of fully sated rats (tail-pinch) would induce the animals to eat. Tail-pinch-induced eating proved to be an extremely reliable and robust phenomenon, which Dr. Antelman and his colleagues were able to demonstrate in a significant percentage of more than 4,000 animals tested. The initial report of the discovery of tail-pinch-induced eating appeared in Science (Antelman and Szechtman, 1975), one of the world's leading scientific journals.

Repeated application of tail-pinch, several times daily, was subsequently shown by Neil Rowland, Ph.D. (Department of Psychology, University of Florida, Gainsville, Fla.) and Dr. Antelman to induce considerable obesity when applied over several days. This work, which also was published in Science (Rowland and Antelman, 1976), demonstrated that the application of tail-pinch six times a day for ten minutes each, over a four to five day period, increased caloric intake two and one-half to more than three-fold, and increased weight more than four-fold compared to control animals not exposed to tail-pinch stimulation. Percentage weight gain in animals given tail-pinch averaged 22% compared to 5% for un-pinched controls. This is equivalent to a 1,000 pound beef cow gaining 220 pounds in less than a week. Interestingly, tail-pinch induced the largest percentage weight gain (23.5% over and above controls) in animals treated with estradiol benzoate, the principal ingredient in several of the hormonal implants marketed commercially in beef cattle markets.

In addition to its ability to increase weight gain in normal animals, tail-pinch is also able to reverse eating deficits due to illness or the anorectic effects of some drugs. Thus, it was shown that tail-pinch could induce eating in rats or cats made aphagic and adipsic (no eating or drinking) by brain lesions of the lateral hypothalamus. Such animals usually die unless tube-fed. Indeed, all but one of the un-pinched controls did die in this rat study while 42% of the animals receiving tail-pinch survived (without tube feeding). These animals recovered to the point of regaining the ability to eat spontaneously. Tail-pinch also reversed the essentially complete akinesia otherwise observed in these animals. It has similarly been shown to reverse the deleterious effects of brain lesions on reproductive behavior (Wang and Hull, 1980).

Since the original report of tail-pinch-induced eating by Antelman and Szechtman, scores of papers on the subject have been published and many highly regarded scientists have become involved in this area of research. The types and species of animals in which eating in response to mild stimulation has been demonstrated is now considerable. Indeed, tail-pinch-induced eating has now been reported in species as primitive as mollusks (e.g., it has been shown in sea slugs—Kavaliers and Hirst, 1980).

The constantly expanding worldwide body of knowledge surrounding tail-pinch-induced enhancement of eating behavior was soon seen to have important applications in the industries engaged in the production of food animals, where more efficient methods for increase in feed intake and weight gain are constantly sought by producers. Early recognition of these potentially lucrative applications for the tail-pinch principle for milk and beef production led scientists to investigate these opportunities through the development and testing of its first devices, called the Animal Behavior Modifer, or "ABM"™.

The original work by Antelman and his colleagues showed that the neurochemical, dopamine, played a key role in the induction of eating and other behaviors by tail-pinch. Dopamine—which is depleted in Parkinson's disease—is now known to be essential for the initiation of motivated behavior in animals such as eating, sexual and maternal behaviors, among others. Subsequent research by others has confirmed and extended the value of tail-pinch stimulation as a non-drug technique for altering brain neurochemistry in animals. For instance, it has now been demonstrated and replicated that tail-pinch reliably releases the neurotransmitters dopamine, serotonin and norepinephrine from the brain cells. It also causes a marked increase in blood flow to the brain. Thus, what started out as a way to get animals to eat on command has turned out be a major contribution to the study of brain neurochemistry. All of this was made possible because tail-pinch is so very reliable in activating brain-behavior connections. In the latter 1970's only a few laboratories in this country were using tail-pinch. In the mid-1990s laboratories all over the world were using the tail-pinch technique to study the actions of neurochemicals.

The application of their findings in accordance with the invention for the non-drug treatment of a host of disorders with a human version of the ABM is discussed below. The logic of treating human disease through the application of this science is based on the findings that behavioral activation via tail-pinch in animals produces effects that may mimic conventional treatments for certain brain diseases.

The advantages of a human-use device, which will be referred to as an HBM (Human Behavior Motivator), relative to drug therapy are substantial. First and foremost, it introduces the concept of Patient Directed Therapy, available on demand, in whatever "dose" is required, on an "as needed" basis. How a person feels at any given moment can vary as a function of changes in either or both the physiological and/or external environments. For example, even healthy people have good days and bad days as well as good and bad periods within the same day. Therefore, every single time a drug is taken, for whatever illness, there is always the potential difficulty of either taking too much relative to an individual's current state and thereby causing undesirable "side effects", or under-dosing and thus failing to alleviate the symptoms of that illness. When such problems occur thee is nothing that a patient can do except wait until the next scheduled drug administration and hope that the problem will then be alleviated. In other words, once a drug is in a person's system, the person is stuck with the consequences, good or bad, and can do little or nothing until they resolve themselves. By contrast, the great advantage of a device such as the HBM is that it's effects can be modified immediately. If the pressure, i.e. "dose", is too high, it can be promptly lowered, or if it is too low it can be raised. When Symptoms worsen or improve, the "dose" can be changed immediately. In short, the patient is no longer captive to a predetermined schedule of drug administration, rather, he or she can now control the agenda on an "as needed" basis. In this way, the danger of any untoward effects are greatly lessened, since therapy is kept to a minimum and taken only as required.

Portability and remote controllability are also important advantages of the HBM relative to drug therapies. Since the device is worn, it is always immediately available for use. For example, one doesn't need to go looking for water in order to take pills. Similarly, the others need not be aware when a patient is administering therapy. In the case of severely disable patients unable to activate a typical remote control device, provision is made for voice activation.

There are about 1.5 million patients with Parkinson's Disease in the United States, Japan and Europe and 2.5 million patients worldwide. The disease is caused by the destruction of a specific nucleus in the brain which contains large quantities of the neurotransmitter dopamine. The main treatment is the drug levodopa used in combination with a related enzyme inhibitor which increase the levels of available dopamine in the brain thereby partially reversing the effects of the disease. There drugs are not usually given until the symptoms become serious because levodopa eventually will cease to be effective after several years of treatment. Anticholinergic drugs which block acetylcholine receptors in the brain are usually given first in the course of treatment and levodopa will usually be introduced when anticholinergics are no longer effective. New drugs which act like dopamine and new types of enzyme blockers which protect dopamine from destruction are under study for treatment of the disease. However, the role of activation in providing symptomatic relief from the akinetic effects of Parkinsonism is well established. Indeed, it has recently been portrayed in the movie "Awakening", based on the book of the same title by the neurologist, Oliver Sachs.

In animals it has been shown and accepted by scientists worldwide that behavioral activation by tail-pinch increases the levels of extracellular dopamine in the nigrostriatal system of the brain. The invention makes possible the treatment of Parkinson's disease in humans.

There are thought to be 20 million depressed people in the U.S.A. As many as 7% of the population may be depressed at some time in their lives and 3% will be severely depressed. In 1994, almost 9 million people sought treatment for depression and as many as 5.5 million people were treated with drugs that year. The most common form of treatment for depression is the use of drugs which block the reuptake of serotonin in the brain, of which class the most often prescribed drug is Prozac. More than 15 million prescriptions are filled each year for depressive disorders but only 10% of the patients go to psychiatrists. The rest are treated by primary care physicians. The most effective drugs in the treatment of depression increase the free levels of the neurotransmitters norepinephrine and serotonin in the brain by blocking their reuptake into brain neurons (Freeman et al, 1993).

The most effective of all antidepressant treatments is not a drug but rather electroconvulsive shock which is a stressful stimulus. This and other non-drug antidepressants such as sleep deprivation, suggest a role for behaviorally activating stimuli in the treatment of depression. It is known that behavioral activation by means of tail-pinch is laboratory animals induces an increase in extracellular serotonin, dopamine and norepinephrine levels in the brain. These neurotransmitters are known to be involved in depression in humans. The commonly used anti-depressant drugs actually increase the levels of these neurotransmitters in the brain by blocking the reuptake of these neurotransmitters into presynaptic cells. Therefore the invention permits behavioral activation in humans which increases the levels of the neurotransmitters in the brain and permits a treatment or adjunctive treatment in depression. The savings in drug costs, not to mention the avoidance of drug side-effects represent a very significant addition to the treatment possibilities in depression. The use of such an activator would be helpful as a treatment used in conjunction with conventional drugs but would also permit the drugs to be used at lower doses where side-effects would be less of a problem.

There are 500,000 victims of stroke each year in the United States. At least 300,000 patients each year will be starting rehabilitation treatment after stroke. New types of drugs are being developed. Among those drugs under development are compounds known to increase cerebral blood flow and extracellular glucose levels in the striatum. Several research articles regarding changes in blood flow and glucose levels with tail-pinch in animals are in the literature. Use of the invention to create such stimulation in humans contributes to the rehabilitation of brain function after stroke injury or could be used to treat ischemic insufficiency.

The human-use device, presently referred to as the "Human Behavior Modifier", or "HBM", is based upon the same principles used in the Animal Behavior Modifier (ABM). The HBM is a pressure-applying apparatus and method used to elicit particular behaviors. It includes a mechanism for mounting the apparatus along the spine, a mechanism for applying variable localized pressures to the spine area, and a device for automatically controlling the variations in pressures applied. The method includes the steps for mounting the pressure-applying apparatus and allowing for the use of variable pressure over time in a predetermined manner. The way for automatically controlling the variations in pressures is obtained using a programmable electronic timing circuit. Included in the electronic timing circuit is a provision for it to randomly program the pressures over time.

The HBM includes a belt and halter which holds the pressure-applying apparatus when the device is mounted along the spine. Another method for mounting the pressure-applying apparatus is an adhesive patch system which holds the device in place. A manual control system is included which allows for the selection of various pressures to be applied automatically over time in a predetermined manner. The manual control includes a shut-off capability which overrides any preprogramming.

In a study undertaken by one or more of the co-inventors, a number of subject were tested using word lists of equal difficultly from the ADAS (Altzheimers Disease Assessment Scale) rating methodology. Subjects were given a word list and given a certain time to study the list. Then they put the list down and were asked to repeat as many words on the list as possible. This portion of the test was repeated in different forms and in each instance, the participants achieved responses in the 95% to 100% correct range.

The participants were then presented with a second word list of equal difficulty accompanied by a major distracting stimulus such white noise. Subjects presented with a major distracting stimulus has a significant increase in the number of errors in repeating the ADAS list. The percent correct decreased from the 95% to 100% range to 30% to 50% range. Using a different list of equal difficulty, the same subjects were then presented with the same major distracting stimulus in the presence of controlled stress as described more hereinafter. The percent correct increased back to the 90% to 95% range in the presence of the controlled stress. Thus, one infers that since the only variable that changed was the presence of controlled stress in humans, the controlled stress resulted in an increase in selective attention abilities, or in the ability to tune out the distracting stimuli.

Figure 1B:
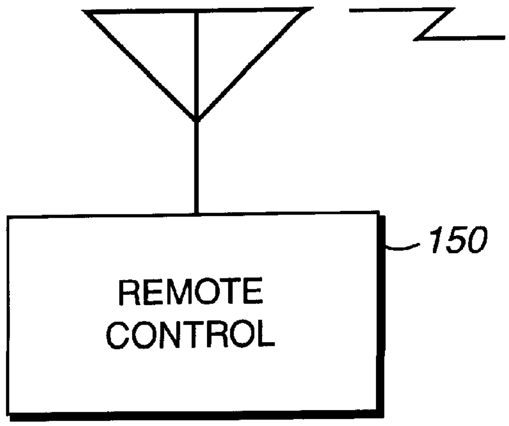
FIG. 1B illustrates an exemplary remote control device for controlling the application of stress or pressure to a human.

FIG. 1A illustrates a belt with shoulder straps for securing a stress inducing device 100 to body of a human. FIG. 1B shows a remote control device for interacting with the unit 100 to control the application of pressure, a form of stress. The shoulder straps 110 shown in FIG. 1A sit on the shoulders like suspenders and the belt 120 straps around the humans body so as to position the stress inducing unit 100 over the spinal column.

Preferably, the shoulder straps are adjustable to permit positioning of the stress inducing unit 100 over different portions of the spinal column in order to achieve different effects on the human body.

Figure 2:
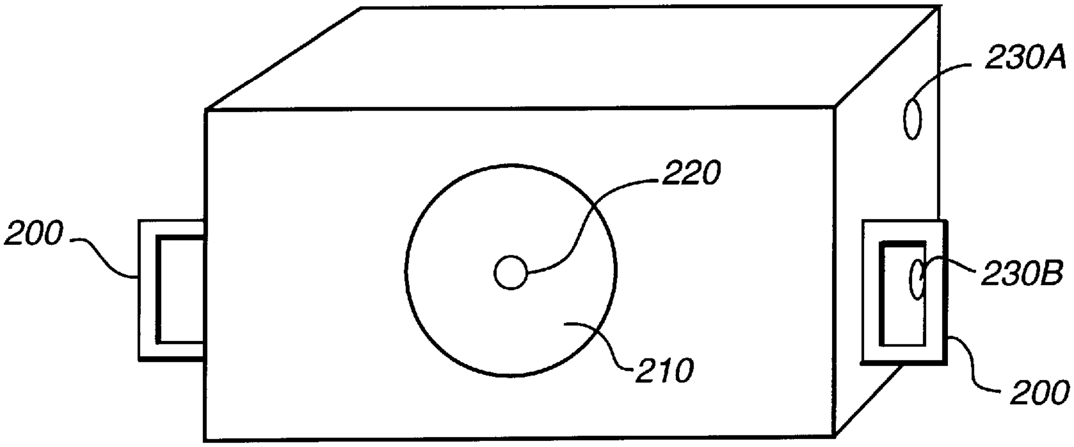
FIG. 2 illustrates the external appearance of an exemplary stress inducing device shown in FIG. 1.

FIG. 2 illustrates the stress inducing unit 100 in more detail. The stress inducing unit 100 is approximately 1½"

high by 1½" deep by 3" long. It has belt loops 200 for connection to the belt shown in FIG. 1B. A pressure head 210 is driven by a servo unit inside the box so as to controllably apply pressure to the spinal area of a human. A pressure sensor 220 is optionally and preferably installed flush with the pressure head 210 so as to sense the pressure being applied against the spinal column for controlled purposes. Control buttons 230A and 230B are provided to enable the human subject to control the amount of pressure in a self administration mode.

Figure 3:
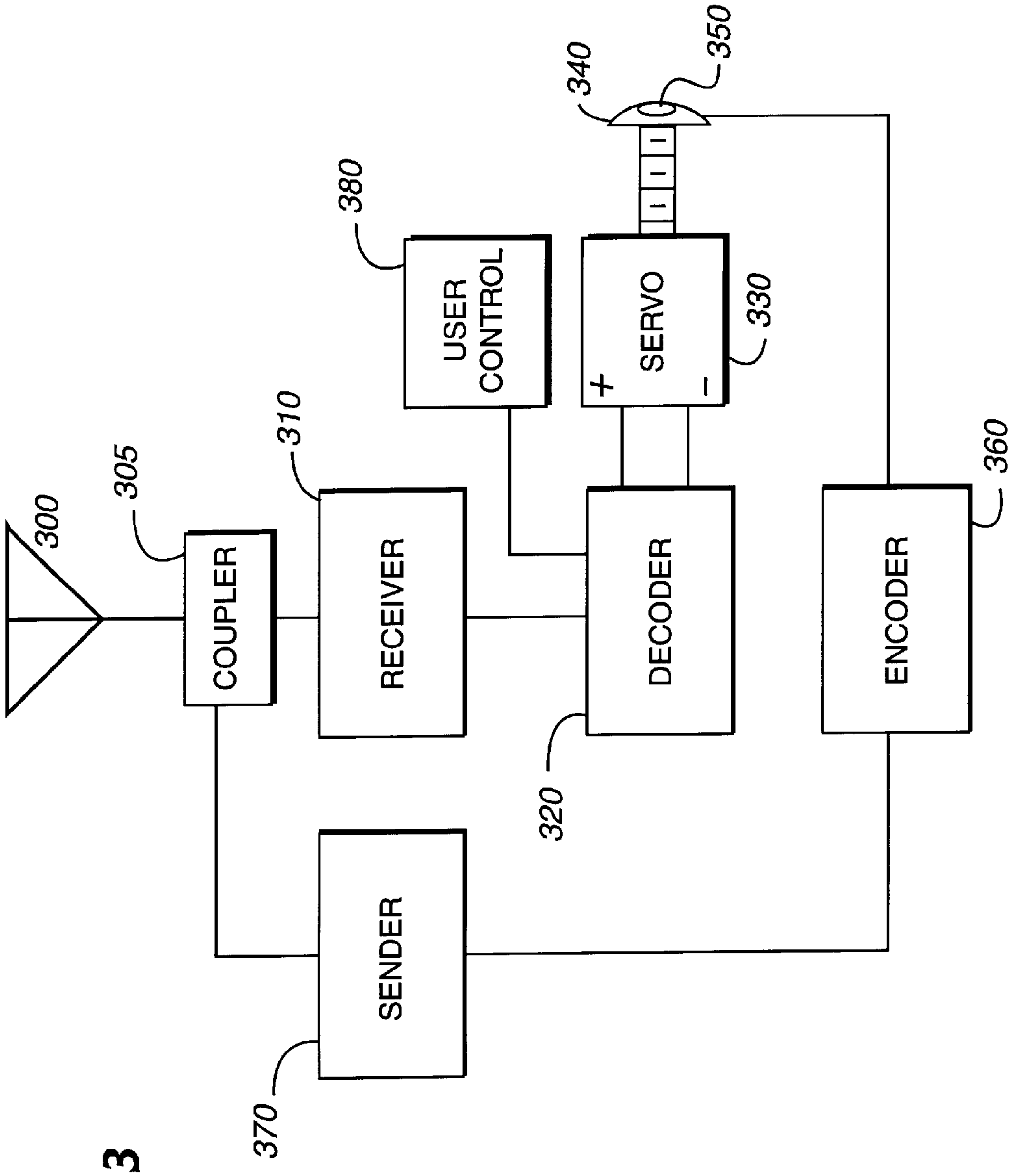
FIG. 3 is a block diagram of the stress inducing device in FIG. 2 and exemplary control circuitry.

FIG. 3 is a block diagram of the stress inducing device shown in FIGS. 1A and 2. As shown in FIG. 3, antenna 300 is utilized for both receiving and transmitting. A duplex coupler or diplex coupler 305 maintains isolation between the sending and receiving paths. Incoming commands from remote controlled device 150 shown in FIG. 1B are forwarded through the coupler 305 to receiver 310 and then to decoder 320 where the various commands are decoded. The two most significant commands involve an increase of pressure shown on line 331 and a decrease of pressure shown on line 332. These lines connect to servo motor 330 and activate server motor 330 to increase or decrease the pressure applied to the spine of the human, respectively. Servo 330 drives a threaded shaft on which is mounted the pressure head 340. In operation, the servo motor causes the pressure head to move inward and outward in a controlled manner, beyond the front of the box or container shown in FIG. 2, to increase or decrease the amount of pressure against the spine. Servo 330 can drive the threaded shaft directly or through an intermediate gear chain depending on obvious design considerations.

A pressure sensor 350 is mounted flush with the surface of the pressure head and is utilized to measure the amount of pressure being applied against the human. That quantity of pressure is encoded in a coder 360 and sent to sender 370 for transmission back to the remote controlled device 150 shown in FIG. 1B. That device will be discussed more hereinafter.

A manual user control 380 is shown in FIG. 3 connected to the decoder for permitting the user to control the amount of pressure manually in response to buttons 230A and 230B shown in FIG. 2.

Figure 4:
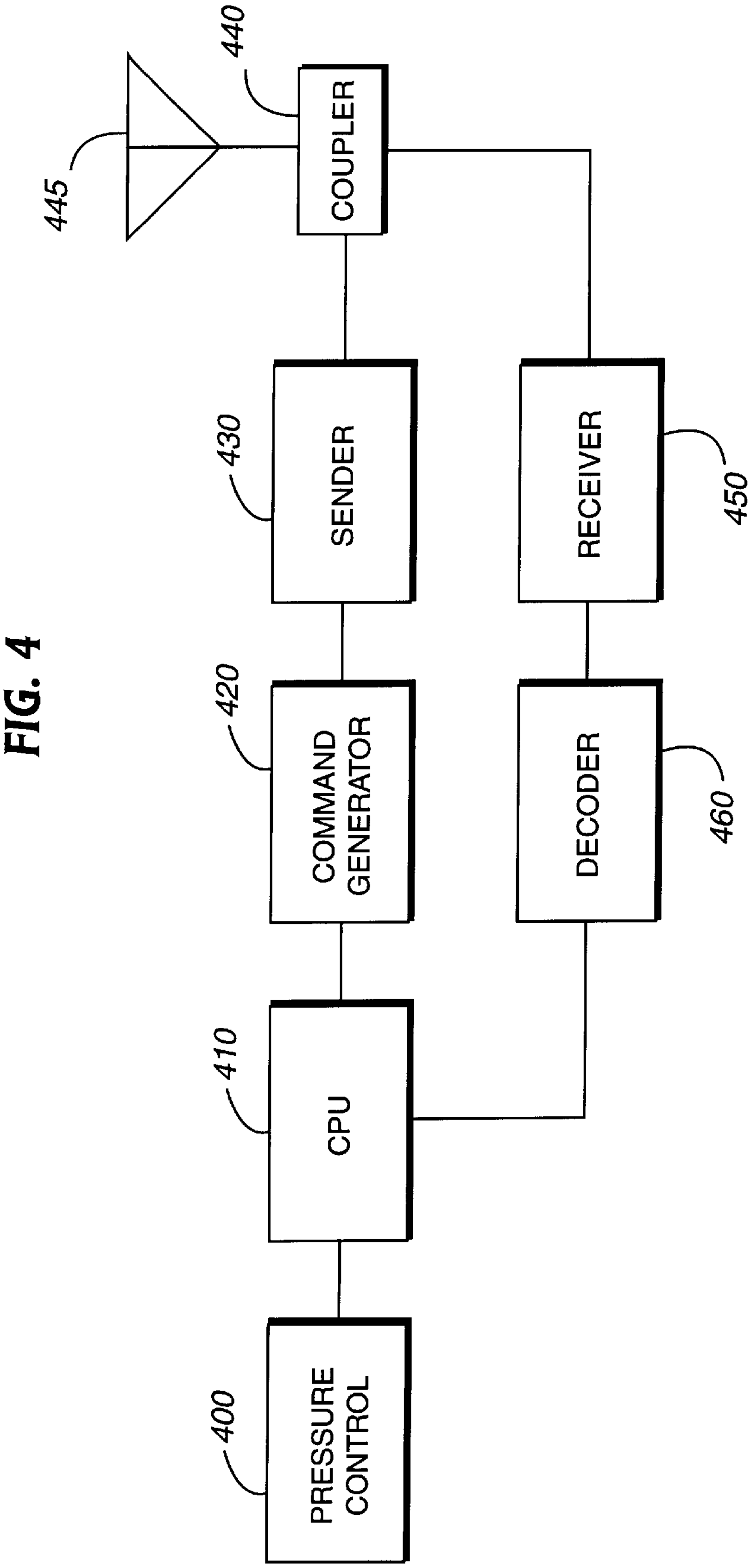
FIG. 4 is a block diagram of an exemplary remote control device shown in FIG. 1B.

FIG. 4 is a block diagram of the remote controlled device 150 shown in FIG. 1B. A pressure control device 400, such as a joy stick or a pair of increase/decrease switches are used to increase or decrease pressure. The control signals generated by the pressure control 400 are applied to CPU 410 which controls the generation of commands by command generator 420 which are sent via sender 430, duplex or diplex coupler 440 and antenna 445 to the belt attached device shown in FIG. 3.

As the pressure increases or decreases, the pressure is detected by pressure sensor 350, shown in FIG. 3 and the value of the pressure sensed is returned by an encoder 360 and sender 370 to antenna 300, all shown in FIG. 3. The radiated return information is received in antenna 445 shown in FIG. 4 and coupled over coupler 440 to receiver 450 and decoder 460 decodes value of the pressure and applies it CPU 410 which uses the sensed pressure for control purposes.

Using the devices shown in these figures, one can reliably position and apply stress to a human to order to achieve the desired affects.

The techniques described above can be utilized to facilitate the treatment of Parkinson's disease, depressive disorders and stroke.

In addition, the application of controlled stress increases coronary blood flow, increases levels of hemoglobin (as a treatment of iron deficiency anemia or general anemia), reduces symptoms of sickle cell anemia, provides a treatment for human sexual disfunction, provides a possibility for fertility treatment without the results of multiple births which often accompany other forms of treatment, is useful in controlling and/or preventing eating disorders such as those which occur in cancer patients, anorexia nervosa or bulemia. The use of the controlled stress results in increased vigilance and improved selective attention and it can be usefully applied in attentional deficit hyperactive disorder for children and adults and in certain diseases such as schizophrenia.

Although the present invention has been described and illustrated in detail, it is clearly understood that the same is by way of illustration and example only and is not to be taken by way of limitation, the spirit and scope of the present invention being limited only by the terms of the appended claims and their equivalents.

What is claimed is:

1. A method of causing a change in the body of a human being, comprising the steps of:

a. positioning a pressure actuator against a portion of the human spine; and b. selectively applying pressure to the spine using said actuator; wherein the change is an increase in appetite.

2. A method of causing a change in the body of a human being, comprising the steps of:

a. positioning a pressure actuator against a portion of the human spine; and b. selectively applying pressure to the spine using said actuator; wherein the change is an increase in sexual activity.

3. A method of causing a change in the body of a human being, comprising the steps of:

a. positioning a pressure actuator against a portion of the human spine; and b. selectively applying pressure to the spine using said actuator; wherein the change is increased blood flow to brain.

4. A method of causing a change in the body of a human being, comprising the steps of:

a. positioning a pressure actuator against a portion of the human spine; and b. selectively applying pressure to the spine using said actuator; wherein the change is an increase of neurotransmitters in the brain.

5. The method of claim 4 in which the increase in neurotransmitters is an increase in dopamine.

6. The method of claim 4 in which the increase in neurotransmitters is an increase in serotonin.

7. The method of claim 4 in which the increase in neurotransmitters is an increase in norepinephrine.

8. A method of treating an abnormal condition in humans comprising the steps of:

a. positioning a pressure actuator against a portion of the human spine; and b. selectively applying pressure to the spine using said actuator; wherein in which the abnormal condition is Parkinson's disease.

9. A method of treating an abnormal condition in humans, comprising the steps of:

a. positioning a pressure actuator against a portion of the human spine; and b. selectively applying pressure to the spine using said actuator; wherein in which the abnormal condition is a depressive disorder.

10. A method of treating an abnormal condition in humans, comprising the steps of:

a. positioning a pressure actuator against a portion of the human spine; and b. selectively applying pressure to the spine using said actuator; wherein in which the abnormal condition is stroke.

11. A method of treating an abnormal condition in humans, comprising the steps of:

a. positioning a pressure actuator against a portion of the human spine; and b. selectively applying pressure to the spine using said actuator; wherein in which the abnormal condition is iron deficiency anemia.

12. A method of treating an abnormal condition in humans, comprising the steps of:

a. positioning a pressure actuator against a portion of the human spine; and b. selectively applying pressure to the spine using said actuator; wherein in which the abnormal condition is general anemia.

13. A method of treating an abnormal condition in humans, comprising the steps of:

a. positioning a pressure actuator against a portion of the human spine; and b. selectively applying pressure to the spine using said actuator; wherein in which the abnormal condition is sickle cell anemia.

14. A method of treating an abnormal condition in humans, comprising the steps of:

a. positioning a pressure actuator against a portion of the human spine; and b. selectively applying pressure to the spine using said actuator; wherein in which the abnormal condition is infertility.

15. A method of treating an abnormal condition in humans, comprising the steps of:

a. positioning a pressure actuator against a portion of the human spine; and b. selectively applying pressure to the spine using said actuator; wherein in which the abnormal condition is an eating disorder.

16. A method of treating an abnormal condition in humans, comprising the steps of:

a. positioning a pressure actuator against a portion of the human spine; and b. selectively applying pressure to the spine using said actuator; wherein in which the abnormal condition is attention deficit hyperactive disorder.

17. A method of treating an abnormal condition in humans, comprising the steps of:

a. positioning a pressure actuator against a portion of the human spine; and b. selectively applying pressure to the spine using said actuator; wherein in which the abnormal condition is schizophrenia.

* * * * *